(12) United States Patent
Meller et al.

(10) Patent No.: US 6,547,561 B2
(45) Date of Patent: *Apr. 15, 2003

(54) DISPOSABLE ANESTHESIA DELIVERY SYSTEM WITH SHORTENED OUTER SLEEVE AND INNER HOLLOW DRILL

(75) Inventors: Moshe Meller, Haifa (IL); Michael Feldman, Toms River, NJ (US)

(73) Assignee: Tulsa Dental Products Inc., Tulsa, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/799,334

(22) Filed: Mar. 5, 2001

(65) Prior Publication Data

US 2001/0014439 A1 Aug. 16, 2001

Related U.S. Application Data

(63) Continuation-in-part of application No. 09/329,022, filed on Jun. 9, 1999, now Pat. No. 6,287,114, and a continuation-in-part of application No. 09/730,345, filed on Dec. 5, 2000.

(51) Int. Cl.$^7$ .............................................. A61G 17/02
(52) U.S. Cl. ......................................... 433/80; 433/165
(58) Field of Search .................... 433/80, 165; 606/80; 604/272

(56) References Cited

U.S. PATENT DOCUMENTS

| | | |
|---|---|---|
| 1,123,730 A | 1/1915 | Greenfield |
| 1,539,637 A | 5/1925 | Bronner |
| 2,317,648 A | 4/1943 | Siqveland |

(List continued on next page.)

FOREIGN PATENT DOCUMENTS

| | | |
|---|---|---|
| GB | 1430092 | 3/1976 |

OTHER PUBLICATIONS

Data Sheet: Wire—NITINOL; p. 131; publication date unknown; www.smallparts.com; e-mail parts@smallparts.com.

Pearce, Jr. "Intraosseous Injection for Profound Anesthesia of the Lower Molar" (1 page).

Cannell Et Al "Intraosseous Injections of Lignocaine Local Anaesthetics" British Dental Journal, vol. 141, Jul. 20, 1976, pp. 48–50.

(List continued on next page.)

Primary Examiner—Ralph A. Lewis
(74) Attorney, Agent, or Firm—Frishauf, Holtz, Goodman & Chick, P.C.

(57) ABSTRACT

An intraosseous delivery apparatus having a drilling member and a sleeve member. The drilling member includes a drill housing, a connecting portion for establishing a connection to a conventional dental drilling apparatus, and a drill extending from the drill housing. The sleeve member includes a sleeve housing, and a hollow sleeve extending from the sleeve housing. The sleeve housing is adapted to be removably engaged with the drill housing such that the drill is inserted into the hollow sleeve. The drill has a length such that when the drill is inserted into the hollow sleeve, a portion of the drill extends beyond the hollow sleeve. As a result, when the drill is used to drill a hole in bone, the drill is inserted deeper into the hole than the hollow sleeve. The hollow sleeve is adapted to be left inserted in the bone when the drill is removed therefrom. The "in place" hollow sleeve is also adapted to receive a syringe needle through which anesthesia may be directly introduced into the bone via an exposed bottom portion of the drilled hole as well as via exposed side-wall portions of the drilled hole. The drill is preferably smooth, and may also be hollow so that debris generated during drilling enters the interior of the drill. In this case, when the hollow drill is removed from the hollow sleeve, the debris within the hollow drill may also be removed. Still further, the drill may be made of a titanium alloy whose flexibility, wearability and cutting ability is greater than that of conventional hardened stainless steel.

24 Claims, 7 Drawing Sheets

U.S. PATENT DOCUMENTS

| | | |
|---|---|---|
| 2,442,033 A | 5/1948 | Brantly et al. |
| 3,406,685 A | 10/1968 | May |
| 3,750,667 A | 8/1973 | Pshenichny et al. |
| 3,778,904 A | 12/1973 | Melde |
| RE27,923 E | 2/1974 | Bentov |
| 3,893,445 A | 7/1975 | Hofsess |
| 4,002,169 A | 1/1977 | Cupler, II |
| 4,021,920 A | 5/1977 | Kirschner et al. |
| 4,193,197 A | 3/1980 | Kuris et al. |
| 4,220,446 A | 9/1980 | Walker |
| 4,306,570 A | 12/1981 | Matthews |
| 4,513,754 A | 4/1985 | Lee |
| 4,678,471 A | 7/1987 | Noble et al. |
| 4,747,824 A | 5/1988 | Spinello |
| 4,787,893 A | 11/1988 | Villette |
| 4,869,717 A | 9/1989 | Adair |
| 4,944,677 A | 7/1990 | Alexandre |
| 4,973,247 A | 11/1990 | Varnes et al. |
| 5,049,150 A | 9/1991 | Cozad |
| 5,057,013 A | 10/1991 | Dillon |
| 5,085,631 A | 2/1992 | Leighton |
| 5,125,838 A | 6/1992 | Seigneurin |
| 5,173,050 A | 12/1992 | Dillon |
| 5,201,656 A | 4/1993 | Sicurelli |
| 5,203,866 A | 4/1993 | Islam |
| 5,261,877 A | 11/1993 | Fine et al. |
| 5,275,563 A | 1/1994 | Cohen et al. |
| 5,304,140 A * | 4/1994 | Kugo et al. |
| 5,312,345 A | 5/1994 | Cole |
| 5,312,375 A | 5/1994 | Gurmarnik |
| 5,341,816 A | 8/1994 | Allen |
| 5,374,270 A | 12/1994 | McGuire et al. |
| 5,389,070 A | 2/1995 | Morell |
| 5,406,940 A | 4/1995 | Melzer et al. |
| 5,423,823 A | 6/1995 | Schmieding |
| 5,423,824 A | 6/1995 | Akerfeldt et al. |
| 5,429,504 A | 7/1995 | Peltier et al. |
| 5,431,655 A | 7/1995 | Melker et al. |
| 5,484,442 A | 1/1996 | Melker et al. |
| 5,489,208 A | 2/1996 | Mandell |
| 5,527,205 A | 6/1996 | Heath et al. |
| 5,554,154 A | 9/1996 | Rosenberg |
| 5,601,559 A | 2/1997 | Melker et al. |
| 5,653,590 A * | 8/1997 | Heath et al. |
| 5,762,639 A | 6/1998 | Gibbs |
| 5,779,708 A | 7/1998 | Wu |
| 5,814,049 A | 9/1998 | Pratt et al. |
| 6,042,585 A * | 3/2000 | Norman |
| 6,135,769 A | 10/2000 | Kwan |
| 6,210,376 B1 * | 4/2001 | Grayson ..................... 604/264 |
| 6,217,561 B1 * | 4/2001 | Gibbs ......................... 604/264 |
| 6,241,710 B1 * | 6/2001 | Van Tassel et al. ......... 604/272 |
| 6,247,928 B1 * | 6/2001 | Meller et al. ................. 433/80 |
| 6,273,715 B1 * | 8/2001 | Meller et al. ................. 433/80 |
| 6,287,114 B1 * | 9/2001 | Meller et al. ................. 433/80 |

OTHER PUBLICATIONS

Liliental "A Clinical Appraisal of Intraosseous Dental Anesthesia", Oral Surg. vol. 39, No. 5, May, 1975, pp. 692–697.

Bourke "Intra–Osseous Anaesthesia", Dent. Anaesthesia And Sedation, vol. 3, No. 2, Jul. 1974, pp. 13–18.

Dorfman "Predictable and Effective Anesthesia Utilizing Intraosseous Injections" (3 pages).

Leonard "The Efficacy of an Intraosseous Injection System of Delivering Local Anesthetic", JADA, vol. 126, Jan., 1995, pp. 81–86.

Magnes "Intraosseous Anesthesia", Anesthesia Progress, Nov. 1968, pp. 264–267.

Garfunkel Et Al. "Intralignamentry–Intraosseous Anesthesia", Int. J. Oral Surg. 1983; pp. 334–339.

Biddulph "Intraosseous Anesthesia For Dental Procedures", The Arizona Dental Journal (2 pages).

* cited by examiner

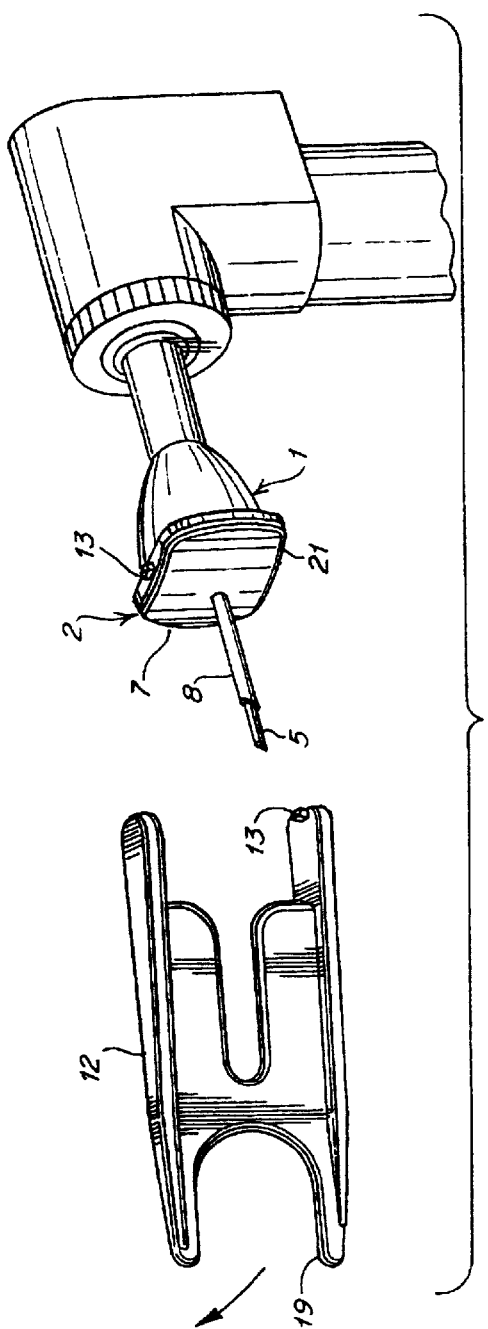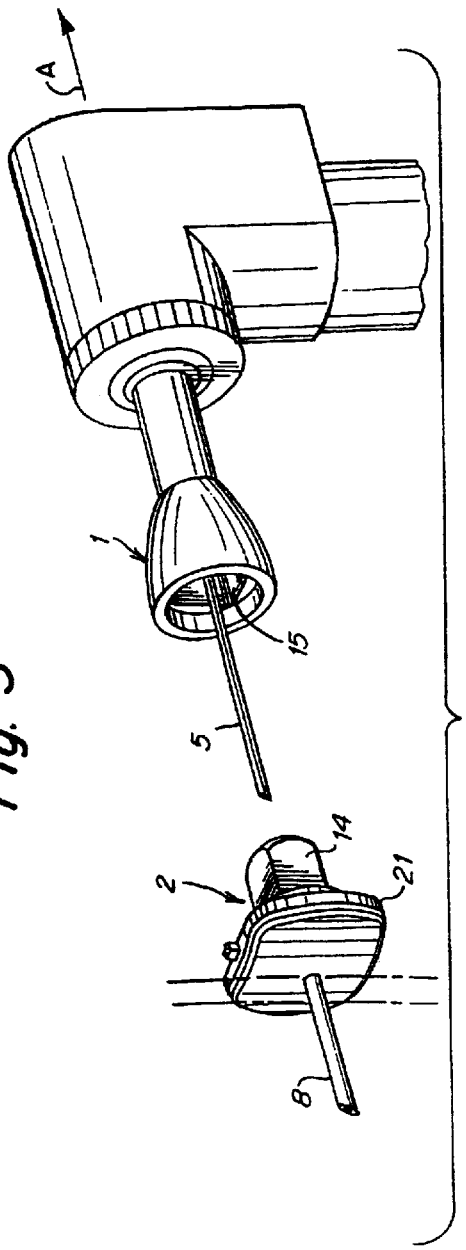

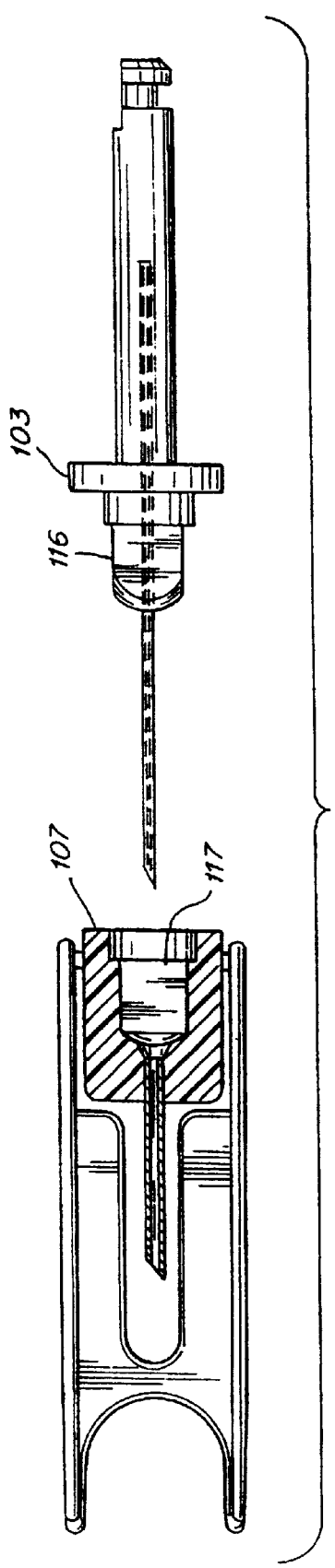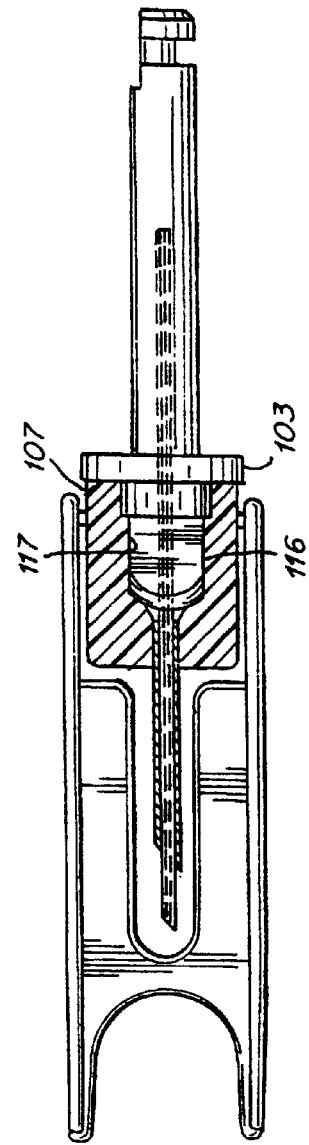
Fig. 6
Fig. 7

DISPOSABLE ANESTHESIA DELIVERY SYSTEM WITH SHORTENED OUTER SLEEVE AND INNER HOLLOW DRILL

This is a Continuation-in-Part Application application Ser. No. 09/329,022 filed Jun. 9, 1999 now U.S. Pat. No. 6,287,114 and application Ser. No. 09/730,345 filed Dec. 5, 2000, the entire contents of both of which are incorporated herein by reference.

BACKGROUND OF THE INVENTION

The present invention relates to an improved disposable delivery system for intraosseously delivering anesthesia to the jawbone or other parts of the living body. In particular, the present invention relates to an improvement of the disposable intraosseous anesthesia delivery apparatus and method disclosed in earlier U.S. application Ser. No. 09/165,010 and earlier PCT application U.S. Ser. No. 99/07728, the entire contents of both of which are incorporated herein by reference.

The present invention is described in detail below with respect to application of dental anesthesia, but the invention is applicable to delivery of anesthesia or other fluids to other parts of a living body, either human or animal. In particular, the present invention is applicable to other surgical procedures such as, for example, orthopedic surgical procedures and/or medical procedures relating to fingers or the nose. Thus, although the invention is described in detail with respect to delivery of dental anesthesia, the invention is not intended to be limited to use only in connection with dental procedures.

In general, anesthesia is delivered by injection of a topical anesthetic followed by a deeper injection of anesthetic for desensitizing nerve endings within the region of interest (infiltration) or for blocking off remote sensory nerves which are coupled to the region of interest (nerve blocking).

It is desirable to minimize the amount of anesthesia injected because toxic reactions may result from drug sensitivity or misdirection of the injection needle into the bloodstream. Such risk of toxic reaction is heightened when repeated administration of anesthesia as required, as is often the case with conventional delivery techniques. In addition, conventional administration of dental anesthesia generally results in numbness of the tongue, cheek, lips and/or even part of the face of the patient for some time after a procedure.

As set forth in U.S. Pat. No. 4,944,677 to Alexandre, conventional methods of delivering dental anesthesia include injection into mucous tissue, injection into a ligament, injection into the septum and injection near a nerve-trunk. However, injection into mucous tissue is disadvantageous because it takes a long time for the anesthesia to take effect (about 5 minutes), because the amount of anesthesia is high (about 4 cc), and because adrenalin or another vaso conductor is required for cardiac patients. Injection into a ligament is disadvantageous because it requires high pressure for injection (which causes pain), because injection is into a septic area, because the risk of infection of the ligament is increased, and because the risk of post-operative problems including inflammation and necrosis is increased. Injection into the septum is disadvantageous because it also requires high pressure for injection (which causes pain), because exact positioning of the needle is required, and because injection is into a septic area. And finally, injection near the nerve-trunk is disadvantageous because there is a long delay in effecting anesthesia (about 10 minutes), because there is a high risk of inadvertent injection into a blood vessel, and because post-operative numbness is very long lasting.

Intraosseous delivery of dental anesthesia directly into the jawbone is also known. Intraosseous delivery is extremely advantageous because it very rapidly achieves numbness limited only to the tooth to be treated, because it enables the amount of anesthetic to be significantly reduced, and because post-operative numbness is essentially avoided. The most relevant prior art intraosseous delivery techniques are described hereinbelow.

U.S. Pat. No. 2,317,648 to Siqveland discloses an intraosseous delivery apparatus and method whereby a threaded sleeve is concentrically and removably positioned around a drill. The drill and threaded sleeve are used together to penetrate the bone, and then the drill is detached and withdrawn, leaving the threaded sleeve embedded in the bone as a guide for a hypodermic needle through which anesthesia may be injected. After injection of anesthesia, the threaded sleeve is withdrawn from the bone by reverse rotation. The threaded sleeve disclosed in Siqveland, however, is too expensive to manufacture to be disposable and must be inserted at a slow speed due to the threading. In addition, the drill disclosed in Siqveland is solid, so that debris which is generated by the drill is left in the drilled hole, thereby reducing absorption of the anesthesia into the jawbone.

U.S. Pat. No. 4,944,677 to Alexandre discloses an intraosseous delivery apparatus and method whereby a smooth, hollow drilling needle is used to drill a hole into the jawbone near the apex of a tooth to be anesthetized. The drilling needle is then removed from the jawbone and a hypodermic needle of substantially the same gauge as the drilling needle is then inserted into the hole formed in the jawbone using a single drop of blood formed during drilling as a marker for entrance to the hole. After the hypodermic needle is inserted into the hole, anesthesia is then delivered by injection directly into the jawbone. This technique, however, is disadvantageous because in actual practice it is very difficult to find the drilled hole and insert the hypodermic needle therein.

U.S. Pat. No. 5,432,824 to Akerfeldt et al discloses a method of accessing a hard tissue whereby a needle drill is inserted into and through a cannula and then used to drill a hole in hard tissue. The distal end of the needle drill has eccentrically shaped tip, so that the drilled hole has a larger diameter than the needle drill and the cannula. After the hole is drilled, the cannula is inserted into the oversized hole. The needle drill is then removed, and the cannula is left secured in the bone to act as a guiding channel for sampling or administration of drugs. The needle drill of Akerfeldt et al, however, has a solid drilling tip, so that as in the case of Siqveland, debris which is generated by the drilling tip of the needle drill is left in the drilled hole. Thus, if the method of Akerfeldt et al were used for the injection of anesthesia, the absorption of the anesthesia would be reduced. In addition, drilling of an enlarged hole as taught by Akerfeldt results in more bone removal, a higher degree of heat generation during drilling, more trauma to the patient, a longer healing time, and a higher risk of infection. Still further, because the hole drilled by Akerfeldt is oversized, the cannula is only loosely fitted in the drilled hole, and injected anesthesia may leak backwards out of the hard tissue.

U.S. Pat. No. 5,762,639 to Gibbs discloses an apparatus and method for intraosseously delivering anesthesia whereby a solid rod is inserted into a perforating catheter, and the assembled rod and perforating catheter are used to perforate ligament or bone tissue. After drilling, the rod is removed and the perforating catheter is left in place to be used as a guide for insertion of a hypodermic needle. In Gibbs, the drilling needle is the outside member (i.e., the perforating catheter), and the rod which is inserted into the perforating catheter is used to prevent debris resulting from drilling from blocking the passage in the perforating catheter. The advantage of this technique is that the perforating catheter remains clear for injection of anesthesia, but the disadvantage is that, as in Siqveland and Akerfeldt et al, the debris which is generated by the drilling is left in the drilled hole, thereby reducing absorption of the anesthesia into the jawbone. And because the drilling needle of Gibbs is the outside member and bottoms in the drilled hole, the bottom portion of the drilled hole is large. As in Akerfeldt et al, this results in more bone removal, a higher degree of heat generation during drilling, more trauma to the patient, a longer healing time, and a higher risk of infection.

All known present day anesthesia delivery devices and methods, moreover, generally utilize a perforating member such as a hypodermic injection needle or drill bit member that is made of hardened stainless steel. Under poor conditions, such hardened stainless steel perforating members may cause significant burning of bone tissue and/or may break. And if either of these events occurs, there is a high risk of infection and/or other complications.

SUMMARY OF THE INVENTION

It is an object of the present invention to provide an improved disposable delivery apparatus and method for intraosseously delivering anesthesia in a simple, easy and effective manner. In particular it is an object of the present invention to provide an improved disposable delivery apparatus and method capable of directly introducing anesthesia into a hole drilled in a bone via an increased exposed bone surface area which is free of drilling debris, while significantly reducing the diameter of the distal end of the drilled hole. Increasing the exposed bone surface area enables greater absorption of the anesthesia, and reducing the diameter of the distal end of the drilled hole results in less bone removal, less heat generation during drilling, less patient trauma, a shorter healing time, and a reduced risk of infection.

In order to achieve the above objects, the intraosseous delivery apparatus of the present invention comprises a drilling member and a sleeve member. The drilling member includes a drill housing, a connecting portion for establishing a connection to a conventional dental drilling apparatus, and a drill extending from the drill housing. The sleeve member includes a sleeve housing, and a hollow sleeve extending from the sleeve housing. The sleeve housing is adapted to be removably engaged with the drill housing such that the drill is inserted into the hollow sleeve. The drill has a length such that when the drill is inserted into the hollow sleeve, a portion of the drill extends beyond the hollow sleeve. As a result, when the drill is used to drill a hole in bone, the drill is inserted deeper into the hole than the hollow sleeve. The hollow sleeve is adapted to be left inserted in the bone when the drill is removed therefrom. The "in place" hollow sleeve is also adapted to receive a syringe needle through which anesthesia may be directly introduced into the bone via an exposed bottom portion of the drilled hole as well as via exposed side-wall portions of the drilled hole. The drill is preferably smooth, and may also be hollow so that debris generated during drilling enters the interior of the drill. In this case, when the hollow drill is removed from the hollow sleeve, the debris within the hollow drill may also be removed.

In addition, it is another object of the present invention to provide an intraosseous anesthesia delivery device whose perforating member has improved flexibility and wearability and improved cutting ability, and which thereby improves operability and reduces the risk of infection and/or other complications. And in order to achieve this object, the present invention provides an anesthesia delivery apparatus which utilizes a bone perforating member made of a titanium alloy that comprises at least 10% titanium.

BRIEF DESCRIPTION OF THE DRAWINGS

FIG. 3 is a perspective view showing the drilling member coupled to a conventional dental drilling apparatus, and a protective member being removed from the sleeve member.

FIG. 4 is a perspective view of the drilling member being removed from the sleeve member.

FIG. 6 is a partial sectional view of an alternative embodiment wherein the drilling member and the sleeve member are adapted to be coupled in a "male/female" configuration opposite to that shown in FIGS. 1–5.

FIG. 7 is a partial sectional view of the drilling member and the sleeve member of FIG. 6 in a connected state.

DETAILED DESCRIPTION

Figure 1:
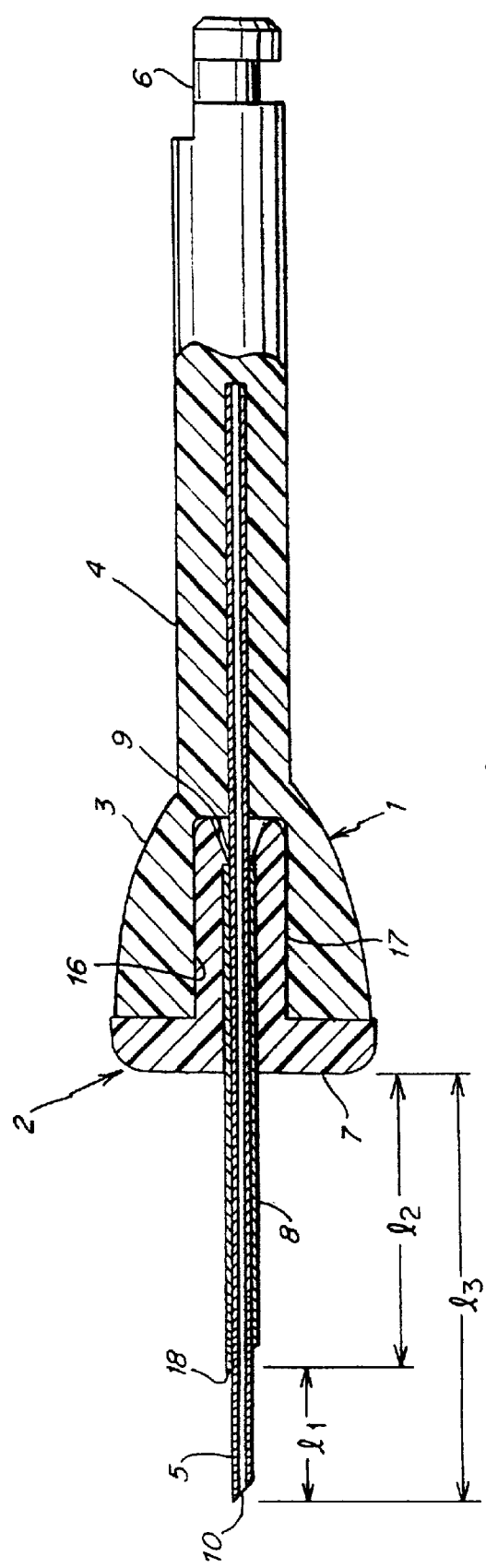
FIG. 1 is a partial sectional view of a drilling member and a sleeve member according to the present invention in an assembled state.

As shown in FIG. 1, the disposable anesthesia delivery apparatus of the present invention comprises a drilling member 1 and a sleeve member 2. The drilling member 1 comprises a drill housing 3, a shaft 4 extending from the drill housing 3, a drill 5 embedded in the shaft 4 and extending through the drill housing 3, and a connecting portion 6 for connecting the drilling member 1 to a conventional dental drilling apparatus. The sleeve member 2 comprises a sleeve housing 7 having a flared opening 9, and a hollow sleeve 8 extending from the sleeve housing 7.

As shown in FIG. 1, the drilling member 1 and the sleeve member 2 may be coupled together such that the drill 5 is inserted into the hollow sleeve 8. The drill 5 has a length such that a portion of the drill 5 extends beyond the hollow sleeve 8 by a length $l_1$. The length $l_1$ may, for example, range from as small as 0.2 mm to about 7 mm. The length $l_1$ is more preferably between about 2 mm and about 4 mm, and is most preferably about 3 mm. The hollow sleeve 8 preferably extends from the sleeve housing 7 by a length $l_2$ of between about 3 mm and about 9 mm, and the hollow sleeve 8 preferably extends from the sleeve housing 7 by a length $l_3$ of between about 9 mm and about 1 mm.

Figure 5:
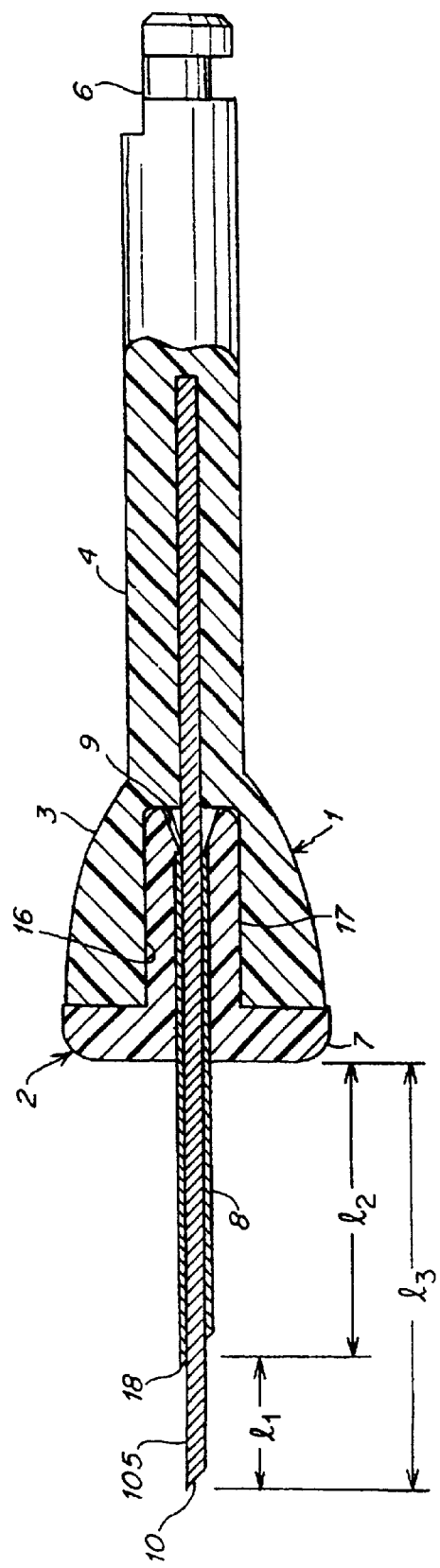
FIG. 5 is a partial sectional view of an alternative embodiment which is identical to the embodiment shown in FIG. 1, except that the drill is solid.

The drill 5 may be hollow as shown in FIG. 1, or solid as shown in FIG. 5, and the drill 5 may also be flexible or rigid. More specifically, the drill 5 may, for example, be a standard stainless steel 27 gauge regular wall needle having an oblique cutting edge 10. Typically, a 27 gauge regular wall needle has an outer diameter of about 0.4 mm, and an inner diameter of about 0.25 mm. Alternatively, as shown in FIG. 5, the drill 105 may be a solid member made of a metal such as surgical stainless steel having substantially the same outer diameter as the hollow drill 5 of about 0.4 mm. Other dimensions for each of the hollow drill 5 and solid drill 105 could also be used.

The drill 5/105 preferably has a smooth outer surface so as to enable a high rotational drilling speed to be utilized and so as to reduce damage to the gums or other tissues during drilling. The drill housing 3, shaft 4 and connecting portion 6, moreover, may be formed of a surgical grade high impact poly-styrene with 20% calcium carbon or another substantially rigid plastic, with the drill 5/105 being insert molded in the shaft 4.

The sleeve 8 may, for example, be a standard syringe-type stainless steel needle having a 23 gauge thin wall. Typically, a 23 gauge regular wall needle has an outer diameter of about 0.62 mm, and an inner diameter of about 0.42 mm. The sleeve 8, like the drill 5/105 preferably has a smooth outer surface, and the sleeve housing 7, like the drill housing 3, may be formed of a surgical grade high impact polystyrene with 20% calcium carbon or another substantially rigid plastic, with the sleeve 8 being insert molded in the sleeve housing 7.

As shown in FIG. 1, the drill housing 3 comprises an opening 16 into which a projecting portion 17 of the sleeve housing 7 may be removably inserted. This coupling may, however, be reversed. That is, as shown in FIGS. 6 and 7, the drill housing 103 may comprise a projecting portion 116 which may be removably inserted into an opening 117 of the sleeve housing 107.

As disclosed in detail in earlier U.S. application Ser. No. 09/165,010 and earlier PCT Application US99/07728, the drilling member 1 and the sleeve member 2 are preferably coupled together in a non-rotational manner. For example, as shown in FIG. 4, the sleeve member 2 may include an essentially square-shaped projection 14 which may be frictionally fitted within an essentially square cross sectional open portion 15 of the drilling member 1. As a result, a rotational driving force may be applied from the conventional dental drilling apparatus via the drilling member 1 to the sleeve member 2. Of course, other mating shapes can be used to achieve the non-rotational coupling and to enable the rotational driving force to be applied from the conventional dental drilling apparatus via the drilling member 1 to the sleeve member 2.

Figure 2:
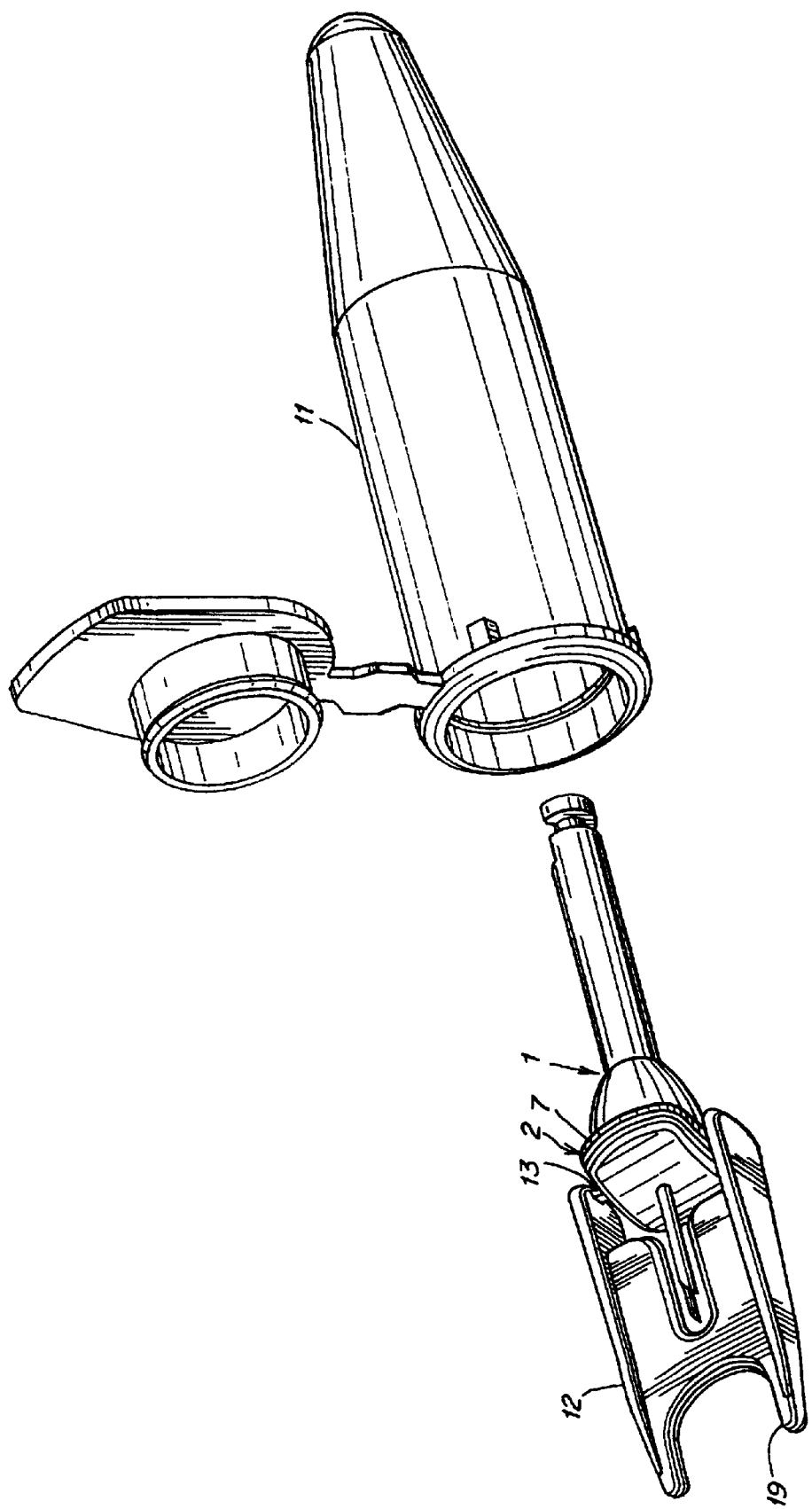
FIG. 2 is a perspective view of the assembled drilling member and sleeve member, and a disposal casing into which the drilling member and sleeve member may be removably inserted.

As shown in FIG. 2, the drilling member 1 and the sleeve member 2 are preferably pre-assembled together and removably stored in a storage and disposal casing 11. A protective member 12 may be removably formed on the sleeve housing 7 via break away points 13. The protective member 12 serves to protect a user from being inadvertently stabbed by the drill 5 and the sleeve 8. After usage, the drilling member 1 and sleeve member 2 may be reinserted into the casing 11 for safe disposal.

As shown in FIG. 3, the assembled drilling member 1 and sleeve member 2 may be removably coupled to a conventional dental drilling apparatus, and the protective member 12 broken away at break away points 13 to expose the sleeve 8 and the drill 5 extending therethrough. The conventional dental drilling apparatus may then be operated to apply a rotational driving force for driving the drill 5 to drill a hole in the jawbone of a patient. In addition, a pressing force may also be applied to assist the drilling operation.

The pressing force and rotational driving force are applied until the flange 16 of the sleeve member 2 presses against or contacts the gums of the patient, thereby ensuring that the drill 5 has been fully inserted in the drilled hole. The surface of the flange 16 is preferably smooth and has rounded edges so as to not to damage the gums or other tissue of the patient during the drilling operation. In addition, the face of the flange 16 is preferably convex, so that the sleeve member 2 can be rockingly leveraged when the sleeve member 2 is later removed from the bone.

As shown in FIGS. 1 and 5, respectively, the drill 5 and drill 105 are dimensioned to substantially fill the hollow sleeve 8. Thus, during drilling, the drill 5/105 serves to prevent cuttings and other debris generated by the drilling from entering between the exterior of the drill 5/105 and the interior of the hollow sleeve 8. As a result, when the drill 5/105 is removed from the hollow sleeve 8, a clear conduit into the interior of the bone of the patient may be established via the hollow sleeve 8.

In addition, if, as shown in FIG. 1, the drill 5 is hollow, as the drill 5 drills the hole in the bone of the patient, at least some of the debris generated by the drilling will enter the interior of the drill 5. As a result, when the drill 5 is removed from the sleeve 8, the debris within the hollow drill 5 may also be removed. This will help to maintain the drilled hole free of debris, so that the anesthesia or other fluid to be injected will be more easily and directly absorbed into the bone.

The conventional dental drilling apparatus is preferably operated to rotate the drill 5/105 at about 20,000 rpm during the drilling procedure. However, speeds of about 10,000 to 25,000 rpm can be used with varying degrees of efficiency. As mentioned hereinabove, such high rotational speeds can be utilized because the drill 5/105 preferably has a smooth outer surface. With the drill 5/105 rotating at such high speeds, the hole in the bone can be quickly and painlessly drilled. Other speeds, for example below 10,000 rpm or above 25,000 rpm can also be used depending upon the specific application.

As the drill 5/105 drills the hole in the bone of the patient, a distal end of the sleeve 8 is caused to ream the drilled hole. This can be achieved in several ways. Namely, since the drilling member 1 and the sleeve member 2 are preferably non-rotationally coupled together, the rotational driving force applied by the dental drilling apparatus to the drilling member 1 will be conveyed to the sleeve member 2 to rotationally drive the distal end of the sleeve 8 to ream the drilled hole. Alternatively and/or additionally, the manual pressing force applied to the drill will cause the distal end of the sleeve 8 to ream the drilled hole. In either or both cases, the reaming action ensures that the distal end of the sleeve 8 will be securely and tightly fitted into the drilled hole.

Once the drilling operation is completed, the drilling member 1 is disengaged from the sleeve member 2 and the drill 5/105 is withdrawn from the sleeve 8. (See, for example, FIG. 4.) This is achieved, for example, by exerting a rearward withdrawal force on the drilling member 1 in the direction of arrow A while the sleeve member 2 is held in place. The sleeve member 2 may be held in place by pressing a specialized dental instrument or the U-shaped end 19 of the protective member. 12 against the flange 16.

Significantly, because the drill 5/105 has a length such that the drill 5 extends beyond the distal end of the sleeve 8 during drilling, the drill 5/105 is inserted deeper into the drilled hole than the distal end of the sleeve 8. As a result, when the drilling member 1 is disengaged from the sleeve member 2 and the drill 5/105 is withdrawn from the sleeve 8, the distal end of the sleeve 8 will only be partly inserted into the drilled hole. That is, the hole will have been drilled deeper than the extent of insertion of the sleeve 8 in the hole. This will leave an increased exposed bone surface area, including the exposed bottom portion of the drilled hole and exposed side-wall portions at the distal end portion of the drilled hole which extends beyond the sleeve 8. As a result, the anesthesia or other fluid to be injected will have a larger surface area through which to be absorbed into the bone.

In addition, because the outer diameter of the drill 5/105 is not greater than the outer diameter of the sleeve 8, the distal end portion of the drilled hole which extends beyond the sleeve 8 will also have a smaller diameter than the outer diameter of the sleeve 8. As a result, the diameter at the distal end of the drilled hole at the inner portion of the bone is reduced, thereby resulting in less bone removal, less heat generation during drilling, less patient trauma, a shorter healing time, and a reduced risk of infection.

After the drilling member 1 is disengaged from the sleeve member 2 and the drill 5/105 is withdrawn from the sleeve 8, a conventional syringe may then be used to inject an anesthetic or other fluid into the interior of the bone via the hollow sleeve 8. More specifically, a syringe needle is inserted through the flared opening 9 of the sleeve member 2 and into the hollow sleeve 8. The syringe needle must, of course, have a gauge which is smaller than the inner diameter of the hollow sleeve 8 so that the syringe needle may be inserted into the hollow sleeve 8. Preferably, a sufficient clearance is provided between the hollow sleeve 8 and the syringe needle such that a build up of pressure is avoided when injecting the anesthetic or other fluid and so that the syringe needle may be easily removed from the hollow sleeve 8. However, the syringe needle should be fitted sufficiently tightly within the hollow sleeve 8 so as to avoid back leakage of injected anesthetic or other fluid therebetween. For example, the syringe needle may, like the drill 5/105, be a standard stainless steel 27 gauge regular wall needle having substantially the same outer diameter as the drill 5/105.

Preferably, the sleeve member 2 projects no more than about 5 mm from the gum surface when the device is used in dental applications. Thus, the sleeve member 2 is sufficiently small and unobtrusive so as not to interfere with the dental procedure which is being performed. In most cases, the sleeve member 2 may be left inserted in the jawbone of the patient throughout the dental procedure. Accordingly, additional anesthetic or other fluid may be applied, if and when necessary, via the hollow sleeve 8 which is left inserted in the bone of the patient.

At the end of the procedure, the sleeve 8 may be removed from the bone of the patient either by manually pulling the housing 7 of the sleeve member 2 or by using a pliers-type or U-shaped tool adapted to grip a portion of the sleeve member 2.

Figure 8:
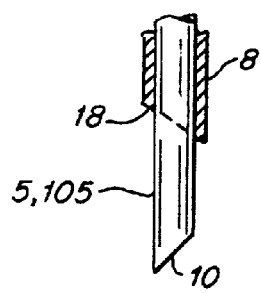
FIG. 8 is a partial sectional view showing an alternative alignment of the leading edges of the drill and the hollow sleeve when the drill is inserted into the sleeve.

As shown in FIGS. 1–7, the cutting edge 10 of the drill 5/105 and the leading edge 18 of the sleeve 8 are oblique and aligned with each other. However, as shown in FIG. 8, the oblique cutting edge 10 and the oblique leading edge 18 may be aligned opposite to each other. The oblique cutting edge 10 and the oblique leading edge 18 are preferably ground 45–20 degrees relative to the longitudinal axes of the drill 5/105 and the sleeve 8, respectively. Other alignments, angles, and/or drilling and reaming edge configurations are also possible.

Figure 9:
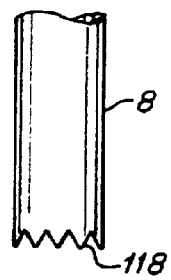
FIG. 9 is an enlarged side view of a portion of a sleeve according to an alternative embodiment wherein the sleeve has a serrated leading edge.
Figure 10:
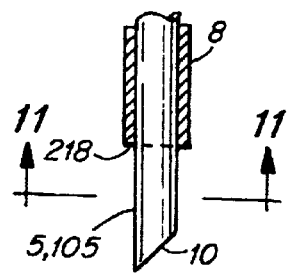
FIG. 10 is a partial sectional view showing another alternative embodiment of the sleeve (with the drill inserted therein) wherein the sleeve has a substantially horizontal leading edge having a rough surface.
Figure 11:
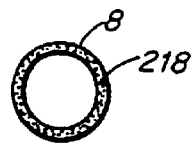
FIG. 11 is an enlarged sectional view taken along line 11—11 shown in FIG. 10 (without showing the drill).
Figure 12:
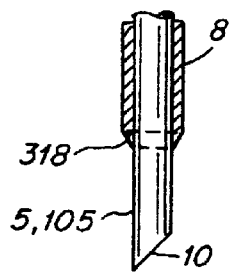
FIG. 12 is a partial sectional view showing another alternative embodiment of the sleeve (with the drill inserted therein) wherein the sleeve has a tapered leading edge having a rough or smooth surface.

As shown in FIG. 9, for example, the sleeve 8 may be provided with a substantially horizontal serrated leading edge 118, or as shown in FIG. 10, the sleeve 8 may be provided with a substantially horizontal leading edge 218 having a rough surface. The rough surface of the leading edge 218 is shown in FIG. 11 (enlarged and without showing the drill 5/105). The rough surface may be formed, for example, by sandblasting or by impact with a sharp or pointed object. In addition, as shown in FIG. 12, the sleeve 8 may be provided with a tapered leading edge 318 having a rough or smooth surface. The advantage of the tapering is that debris generated during drilling may be deflected backward away from the drilled hole.

Figure 13:
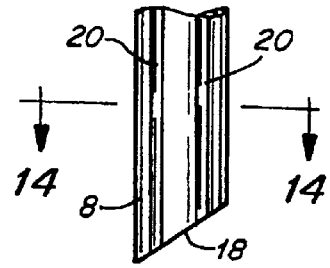
FIG. 13 is a side view of a portion of a sleeve according to another alternative embodiment wherein the sleeve has grooves formed on an outer surface thereof.
Figure 14:
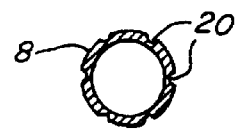
FIG. 14 is a sectional view taken along line 14—14 shown in FIG. 13.

As described hereinabove, the sleeve 8 preferably has a smooth outer surface. However, as shown in FIG. 13 and 14, the sleeve 8 may have grooves 20 formed on the outer surface thereof. The grooves 20 may be provided to assist removal of the debris generated during drilling out of and away from the drilled hole.

Figure 15:
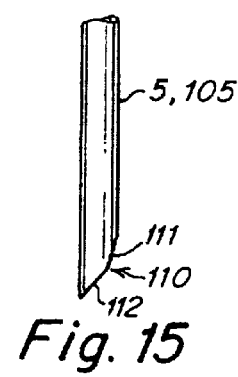
FIG. 15 is an enlarged side view of a drill having a compound oblique cutting edge surface.

Still further, as shown in FIG. 15, the drill 5/105 may have a cutting edge 110 having a compound oblique surface made up of surface portions 111 and 112 which have different angles relative to the longitudinal axis of the drill 5/105.

Other combinations of the above described oblique, compound oblique, substantially horizontal, rough, smooth and/or tapered leading and cutting edges are also possible.

According to the present invention as described hereinabove, a direct, reusable communication path is established and maintained into the bone of the patient which enables simple injection and/or re-injection of anesthetic or other fluid directly into the bone via an increased exposed surface area in the bone which is free of drilling debris. The anesthetic or other fluid can therefore be more efficiently absorbed directly into the bone, so that the dosage can be reduced while at the a same time producing a more rapid and shorter term effect. According to the present invention, moreover, even though the absorption area is increased, the diameter of the distal end of the drilled hole is reduced, thereby resulting in less bone removal, less heat generation during drilling, less patient trauma, a shorter healing time, and a reduced risk of infection.

Still further, according to another aspect of the present invention, the drill may be made of a material containing titanium whose flexibility, wearability and cutting ability is greater than that of conventional hardened stainless steel. Namely, the drill may be made of a titanium alloy that comprises at least 10% titanium. Preferably, the drill is made of a titanium alloy that comprises at least 40% titanium. For example, according to a preferred embodiment, the drill may be made of a NITINOL alloy whose composition is typically 55%–56% nickel and 44%–45% titanium.

In one specific preferred embodiment, the alloy consists of 44% titanium and 56% nickel and no other appreciable amount of any other ingredient which could adversely effect the purity required for dental instruments.

Still more specifically, the drill of the present invention may be made, for example, from NITINOL Type 1, Part No. U-NW-015 available at www.smallparts.com.

The present invention, however, may utilize any material containing titanium whose flexibility, wearability and cutting ability is greater than that of conventional hardened stainless steel.

The use of a titanium alloy achieves numerous significant advantageous effects.

Figure 16:
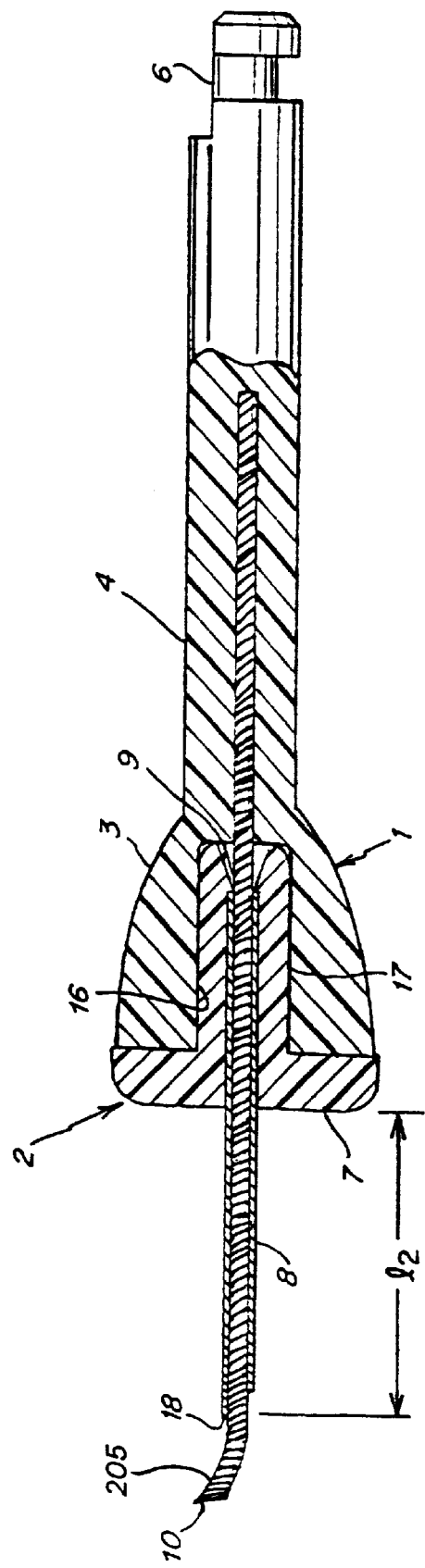
FIG. 16 is a partial sectional view of another embodiment wherein the drill is made of a titanium alloy and a tip thereof is in a bent state.

First, the flexibility and wearability of the perforating member is increased, thereby reducing its chances of breakage. FIG. 16, for example, shows the tip of a drill 205 made of a material containing titanium in a bent state. In fact, when the drill 205 is made of a titanium alloy, it may change direction during drilling and still hit its target, even if from the side and it may do so without breaking and without losing the ability to be disengaged from the sleeve.

Second, the cutting ability of a titanium alloy drill is much higher than that of a conventional stainless steel drill, and the friction between a titanium alloy drill and the bone tissue, into which the drill is being drilled is significantly reduced. This reduces the temperatures generated during drilling and lowers the amount of bone tissue burning, thereby reducing the chances of infection and/or other complications.

Third, the use of a titanium alloy drill significantly reduces the possibility that the inner drill will stick to the outer sleeve after drilling is performed in a manner which would prevent the inner drill from being pulled out of the outer sleeve. This is because the use of a titanium alloy drill essentially eliminates deformation of the inner drill during drilling, and reduces the amount of friction between the inner drill and the outer sleeve during the operation of pulling out the inner drill from the outer sleeve. Thus, after drilling is performed, it becomes much easier to withdraw the inner drill from the outer sleeve in a manner which leaves the outer sleeve in place in the jawbone of the patient. By contrast, when the inner drill is made of stainless steel, there is a risk that the inner drill will be deformed during drilling and that the diameter of the inner drill will be increased. As a result, when the inner drill is made of stainless steel, there is a risk that the inner drill and outer sleeve will stick together in a manner such that it will become impossible to pull the inner drill out of the outer sleeve. And if this happens, the sleeve has to be pulled out of the jawbone of the patient along with the drill, thereby resulting in a wasted procedure. The use of a titanium alloy drill significantly reduces the possibility of this happening.

Fourth, the use of a titanium alloy drill enables drilling to be performed in a much wider range of speeds than is available when a conventional hardened stainless steel drill is used. More specifically, the use of a titanium alloy drill enables drilling to be performed at speeds between approximately 2000 rpm and approximately 20,000 rpm, with a preferred speed of approximately 10,000 rpm, whereas the use of a conventional hardened stainless steel drill typically requires higher speeds on the order of 15,000 rpm.

As shown in FIG. 16, the drill 205 is solid, but the present invention also equally applies to the case where the perforating member is hollow. And in this connection, it is noted that the embodiment shown in FIG. 16 is identical to the embodiment shown in FIG. 5, except that the drill 205 is made of a titanium alloy—and the tip thereof is shown in a bent state.

In addition, it is noted that outer (hollow) sleeve 8 shown in FIG. 16 may also be made of a titanium alloy, or may alternatively be made of conventional hardened stainless steel.

Additional advantages and modifications will readily occur to those skilled in the art. Therefore, the invention in its broader aspects is not limited to the specific details, representative devices, and illustrated uses and examples shown and described herein. Accordingly, various features of the respectively disclosed embodiments can be used with other embodiments, and various modifications and combinations may be made without departing from the spirit or scope of the general inventive concept of the present invention as defined by the appended claims and their equivalents. In particular, it is pointed out that in all the embodiments shown in the drawings, the drill may be solid or hollow.

What is claimed is:

1. A dental apparatus for intraosseously delivering dental anesthesia comprising:

a drilling member including a drill housing, a connecting portion for establishing a connection to a dental drilling apparatus, and a drill extending from the drill housing; and a sleeve member including a sleeve housing, and a hollow sleeve extending from the sleeve housing;

wherein the sleeve housing is adapted to be removably engaged with the drill housing such that the drill is inserted into the sleeve;

wherein the drill is made of a titanium alloy comprising at least 10% titanium and has a length such that when the drill is inserted into the hollow sleeve, a portion of the drill extends beyond the hollow sleeve;

wherein the drill and the hollow sleeve are rotatable by the dental drilling apparatus, the drill comprises a cutting edge that drills a hole in bone, and the hollow sleeve comprises a leading edge that reams a proximal portion of the hole drilled by the drill;

wherein the hollow sleeve is adapted to receive a syringe needle when the sleeve housing and the drill housing are disengaged and the drill is removed from the hollow sleeve; and wherein the drill is solid and has a smooth outer surface.

2. The dental apparatus according to claim 1, wherein the drill is dimensioned to substantially fill the hollow sleeve.

3. The dental apparatus according to claim 1, wherein the drill has an outer diameter of about 0.4 mm, and wherein the hollow sleeve has an inner diameter of about 0.42 mm and an outer diameter of about 0.62 mm.

4. The dental apparatus according to claim 1, wherein the length of the drill is such that when the drill is inserted into the hollow sleeve, the drill extends about 0.3 mm beyond the hollow sleeve.

5. The dental apparatus according to claim 4, wherein the cutting edge of the drill and the leading edge of the hollow sleeve are both oblique.

6. The dental apparatus according to claimed 4, wherein the leading edge of the hollow sleeve is roughened or serrated.

7. The dental apparatus according to claim 4, wherein the leading edge of the hollow sleeve is tapered.

8. The dental apparatus according to claim 1, wherein the hollow sleeve has a smooth outer surface.

9. The dental apparatus according to claim 1, wherein the hollow sleeve has grooves formed along an outer surface thereof in a longitudinal direction.

10. The dental apparatus according to claim 1, wherein the hollow sleeve is adapted to receive a syringe needle having substantially a same outer diameter as the drill.

11. The dental apparatus according to claim 1, wherein the drill housing and the sleeve housing are formed of a plastic material, and the drill and the hollow sleeve are insert molded in the drill housing and the sleeve housing, respectively.

12. The dental apparatus according to claim 1, wherein the titanium alloy comprises at least 40% titanium.

13. The dental apparatus according to claim 1, wherein the titanium alloy is a NITINOL alloy comprising 55%–56% nickel and 44%–45% titanium.

14. The dental apparatus according to claim 1, wherein the titanium alloy consists of 44% titanium and 56% nickel and no other appreciable amount of any other ingredient.

15. A dental method of intraosseously delivering dental anesthesia comprising the steps of:
removably coupling a drilling member and a sleeve member such that a drill housing of the drilling member and a sleeve housing of the sleeve member are removably engaged, and such that a solid drill having a smooth outer surface and extending from the drill housing is inserted into a hollow sleeve extending from the sleeve housing;
removably engaging a connecting portion of the drilling member to a dental drilling apparatus;
operating the dental drilling apparatus to cause the drill to drill a hole in a bone and the hollow sleeve to ream the drilled hole, thereby inserting the drill and the hollow sleeve into the bone, said drill having a length such that a portion thereof extends beyond the hollow sleeve and is inserted deeper into the drilled hole than the hollow sleeve;
disengaging the drill housing and the sleeve housing such that the drill is removed from the hollow sleeve and the hollow sleeve is left inserted in the bone;
inserting a syringe needle into the hollow sleeve left inserted in the bone; and
introducing a fluid from the syringe needle directly into the bone via an exposed bottom portion of the drilled hole as well as via exposed side-wall portions at a distal end of the drilled hole;
wherein the drill is made of a titanium alloy comprising at least 10% titanium.

16. The dental method according to claim 15, wherein the drill is inserted into the hollow sleeve so as to extend about 3 mm beyond the hollow sleeve.

17. The dental method according to claim 15, wherein the drill is operated to drill the hole such that the distal end of the drilled hole has a diameter which is smaller than an outer diameter of the hollow sleeve.

18. The dental method according to claim 17, wherein the hollow sleeve remains inserted in the bone throughout a dental procedure, and wherein fluid is repeatedly injected directly into the bone, if and when necessary, during the dental procedure.

19. The dental method according to claim 15, further comprising a step of removing the needle of the syringe from the hollow sleeve in a manner such that the hollow sleeve remains inserted in the bone.

20. The dental apparatus according to claim 1, wherein the drill and the hollow sleeve are adapted to be rotated by the dental drilling apparatus at a rotation speed of about 2,000 to 20,000 rpm.

21. The dental method according to claim 15, wherein the dental drilling apparatus is operated at a rotation speed of about 2,000 to 20,000 rpm.

22. The method according to claim 15, wherein the titanium alloy comprises at least 40% titanium.

23. The dental method according to claim 15, wherein the titanium alloy is a NITINOL alloy comprising 55%–56% nickel and 44%–45% titanium.

24. The dental method according to claim 15, wherein the titanium alloy consists of 44% titanium and 56% nickel and no other appreciable amount of any other ingredient.

* * * * *